(12) United States Patent
Fischer (10) Patent No.: US 8,398,397 B2
(45) Date of Patent: Mar. 19, 2013

(54) DENTAL INTRALIGAMENTARY INJECTION NEEDLES AND RELATED METHODS OF MANUFACTURE

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 627 days.

(21) Appl. No.: 12/398,039

(22) Filed: Mar. 4, 2009

(65) Prior Publication Data

US 2009/0234288 A1 Sep. 17, 2009

Related U.S. Application Data

(60) Provisional application No. 61/035,967, filed on Mar. 12, 2008, provisional application No. 61/035,977, filed on Mar. 12, 2008.

(51) Int. Cl.
*A61C 5/02* (2006.01)
(52) U.S. Cl. ............ 433/81; 604/117; 604/264
(58) Field of Classification Search .......... 604/112, 604/117, 264; 433/80–81, 224
See application file for complete search history.

(56) References Cited

U.S. PATENT DOCUMENTS

| | | | |
|---|---|---|---|
| 4,472,141 A | 9/1984 | Dragan | |
| 4,512,768 A | 4/1985 | Rangaswamy | |
| 4,767,407 A | 8/1988 | Foran | |
| 4,944,677 A * | 7/1990 | Alexandre | 433/165 |
| 5,514,113 A | 5/1996 | Anderson et al. | |
| 6,113,574 A | 9/2000 | Spinello | |
| 6,273,715 B1 | 8/2001 | Meller et al. | |
| 6,334,856 B1 | 1/2002 | Allen et al. | |
| 6,560,975 B1 * | 5/2003 | Weldon | 62/117 |
| 6,611,707 B1 | 8/2003 | Prausnitz et al. | |
| 6,743,211 B1 * | 6/2004 | Prausnitz et al. | 604/239 |
| 6,767,341 B2 | 7/2004 | Cho | |
| 6,881,203 B2 | 4/2005 | Delmore et al. | |
| 6,908,453 B2 | 6/2005 | Fleming et al. | |
| 6,918,892 B2 | 7/2005 | Martin | |
| 6,924,087 B2 | 8/2005 | Yeshurun et al. | |
| 7,077,830 B2 | 7/2006 | Higaki et al. | |

(Continued)

FOREIGN PATENT DOCUMENTS

| | | |
|---|---|---|
| AU | 2094383 | 6/1984 |
| JP | 2002-315828 | 10/2002 |

(Continued)

OTHER PUBLICATIONS

Mark N. Hochman, Single Tooth Anesthesia: Pressure-Sensing Technology Provides Innovative Advancement in the Field of Dental Local Anestesia, Apr. 2007, AEGIS, pp. 1-9.

(Continued)

*Primary Examiner* — Nicholas Lucchesi
*Assistant Examiner* — Melissa A Snyder
(74) *Attorney, Agent, or Firm* — Workman Nydegger (57) ABSTRACT

Injection needle devices for administering a local anesthetic into tough, dense ligamentary tissue surrounding a tooth. The injection needle is a two-part needle that includes a proximal needle portion formed of metal, ceramic or rigid plastic and a distal needle portion formed of ceramic or hardened metal. The distal penetrating needle portion has an exposed length not more than about 8 mm, and an maximum outside diameter of about 25 gauge. At the transition between the proximal needle portion and the distal needle portion there can be an abrupt stop surface for limiting penetration through tissue. Alternatively, the proximal needle portion can have a tapered surface that permits penetration of the tapered surface into tissue. The injection needle device is designed to minimize pain and prevent buckling of the distal needle portion.

31 Claims, 9 Drawing Sheets

U.S. PATENT DOCUMENTS

| | | |
|---|---|---|
| 7,273,474 B2 | 9/2007 | Chang et al. |
| 2003/0135167 A1 | 7/2003 | Gonnelli |
| 2003/0208138 A1 | 11/2003 | Olson |
| 2003/0208167 A1 | 11/2003 | Prausnitz et al. |
| 2003/0236506 A1 | 12/2003 | Schofield et al. |
| 2004/0049164 A1 | 3/2004 | Patrick et al. |
| 2004/0064109 A1 | 4/2004 | Klint et al. |
| 2004/0106904 A1 | 6/2004 | Gonnelli et al. |
| 2004/0186419 A1 | 9/2004 | Cho |
| 2005/0096603 A1* | 5/2005 | Ooyauchi .................... 604/239 |
| 2005/0245877 A1 | 11/2005 | Wilkinson et al. |
| 2006/0084942 A1 | 4/2006 | Kim et al. |
| 2007/0016149 A1 | 1/2007 | Hunn et al. |
| 2007/0129691 A1 | 6/2007 | Sage, Jr. et al. |
| 2007/0161964 A1 | 7/2007 | Yuzhakov |
| 2007/0233016 A1 | 10/2007 | Kuo et al. |
| 2007/0256289 A1 | 11/2007 | Tamura et al. |
| 2007/0282265 A1 | 12/2007 | Shigematsu et al. |
| 2008/0009811 A1 | 1/2008 | Cantor |
| 2008/0015521 A1 | 1/2008 | Alchas |
| 2008/0015522 A1 | 1/2008 | Yeshurun et al. |
| 2008/0200883 A1 | 8/2008 | Tomono |

FOREIGN PATENT DOCUMENTS

| | | |
|---|---|---|
| JP | 2005-246595 | 9/2005 |
| WO | 2008-011625 | 1/2008 |

OTHER PUBLICATIONS

E.L. Pashley et al., Pressure Created by Dental Injections, Oct. 1981, J Dent Res. 60(10), 1742-1748.

Office Action dated Oct. 8, 2009 U.S. Appl. No. 12/398,061.

U.S. Appl. No. 12/398,061, filed Mar. 4, 2008, Fischer.

U.S. Appl. No. 12/398,039, filed Mar. 4, 2009, Fischer.

Hochman, "Single-Tooth Anesthesia: Pressure-Sensing Technology Provides Innovative Advancement in the Field of Dental Local Anesthesia", Apr. 2007, www.compendiumlive.com/issues/articles/2007-04_05.asp.

Ovsianikov et al., "Two Photon Polymerization of Polymer-Ceramic Hybrid Materials for Transdermal Drug Delivery", Int. J. Appl. Ceram. Technol., 4[1] 22-29 (2007).

Nixing the Need for the Needle, Kristen Philipkoski, Mar. 28, 2006, http://www.wired.com/medtech/health/news/2006/70363.

\* cited by examiner

DENTAL INTRALIGAMENTARY INJECTION NEEDLES AND RELATED METHODS OF MANUFACTURE

CROSS REFERENCE TO RELATED APPLICATIONS

This application claims the benefit of the following: U.S. Provisional Application No. 61/035,967, filed Mar. 12, 2008, and entitled "DENTAL INTRALIGAMENTARY INJECTION NEEDLES AND RELATED METHODS OF MANUFACTURE" and U.S. Provisional Application No. 61/035,977, filed Mar. 12, 2008, and entitled "METHOD OF DENTAL INTRALIGAMENTARY INJECTION USING AN ARRAY OF MICRO-NEEDLES". The disclosures of the foregoing applications are incorporated herein in their entirety.

BACKGROUND OF THE INVENTION

1. The Field of the Invention

The present invention relates to devices for injecting a local anesthetic into the body of a patient for local infiltration, particularly for injecting a local anesthetic into very tough, dense ligamentary tissue surrounding a tooth or teeth prior to work by a dental practitioner (e.g., extraction of a tooth, cleaning of a root canal, or other procedure).

2. The Related Technology

Operative dentistry often requires local anesthesia prior to performing the procedure. More than half of the teeth in the oral cavity can be effectively anesthetized locally by infiltrating an anesthetic composition near the location of the tooth root apexes. Because of the pain associated with such procedures, it is desirable to first administer a topical anesthetic (e.g., benzocaine) adjacent the tooth followed by injection of a local anesthetic (e.g., lidocaine) to the tooth via local infiltration, an intraligamentary procedure, or by remote nerve block. For local infiltration and intraligamentary procedures, a small diameter needle is typically used. In recent years, it has been found that the smaller the diameter and sharper the point of the needle, the less painful is the resulting injection. Because of this, very small needles are sometimes used when administering a local anesthetic adjacent the base of a tooth prior to such work. Unfortunately, because of the very tough and dense nature of the ligamentary tissue into which the needle is pressed and the close proximity of the bone to the root surface, small diameter needles will often bend or "noodle" when attempting to push the needle into the tissue. In addition, as small as these needles are, they are nevertheless large enough to induce pain because of the rich supply of very sensitive nerves within the oral cavity. Although it might be thought that the use of even smaller needles might further reduce pain, the use of such needles is not practical because of their even greater tendency to bend upon attempting to push them through tough, dense tissue.

In addition, it can be very difficult to maintain the needle at a constant depth while attempting to inject the local anesthetic, as very high fluid pressures must be applied manually by the practitioner in order to effectively inject the anesthetic into the dense, tough ligamentary tissue. For example, fluid pressures of hundreds of pounds per square inch ("psi") may be required during injection, which can make it very difficult to hold the needle steady and avoid pushing the needle further into the tissue, risking contact or penetration into the periosteum or bone covering adjacent the tooth root, which is very sensitive. Additionally, existing lever type injection syringes can be clumsy to align, and can easily cause rocking motions when delivering the anesthetic. Finally, they are relatively costly, particularly to clinicians practicing in third world countries.

In addition, current methods of injecting local anesthetic adjacent a tooth via local infiltration and conventional nerve blocks are rather complicated, requiring a significant amount of education and practice to perform them correctly and effectively. Some practitioners, particularly in third world countries, simply do not learn the techniques, but rather will perform a root canal, extraction, or other operative dental work without any anesthesia, which causes the procedure to be extremely painful from the perspective of the patient.

Therefore, what is needed is a needle device that can minimize pain during penetration into the tissue at the base of the tooth, but which will also minimize the tendency of the needle to bend or buckle during insertion as a result of the dense and tough nature of the ligamentary tissue. It would be a further advantage if such a needle device could be employed in simplified methods of applying local anesthesia so that practitioners could more easily learn and effectively utilize such a technique.

BRIEF SUMMARY OF THE INVENTION

The present invention is directed to specialized two-part injection needle devices for administering a local anesthetic into the very tough, dense ligamentary tissue surrounding a tooth. The two-part needle includes a proximal needle portion formed of a rigid material and a distal needle portion formed of ceramic or a high hardness metal. The proximal and distal needle portions are rigidly affixed to each other so that one cannot slide relative to the other. According to one embodiment, the distal needle portion includes an embedded section disposed within a hollow interior of the proximal needle portion and an exposed section extending distally beyond the proximal needle portion. In this way, the distal and proximal needle portions form a telescoping relationship. At least a portion of the embedded section of the distal needle portion may form a friction fit with a hollow interior of the proximal needle portion.

The distal needle portion has an exposed length of not more than about 8 mm, and a maximum outside diameter of about 25 gauge or less. The proximal needle portion has a minimum outside diameter that is greater than the maximum outside diameter of the distal needle portion where the two intersect so as to provide increased rigidity of the proximal needle portion and prevent or inhibit undesired bending or noodling of the distal needle portion when inserted into tough intraligamentary tissue.

The transition between the proximal needle portion and the exposed section of the distal needle portion may provide an abrupt increase in diameter that acts as a stop (or "abrupt stop surface") that limits penetration of the two-part needle through gingival tissue. The abrupt stop surface inhibits or prevents penetration of the proximal needle portion through gingival tissue. The abrupt stop surface can advantageously aid the practitioner in piercing the tissue only to a maximum depth substantially equal to the length of the distal needle portion. Because the exposed length of the distal needle portion is no longer than about 8 mm, and the outside diameter is about 25 gauge or less, pain and discomfort to the patient are minimized during injection of a local anesthetic. The relatively short length of the exposed distal needle portion, coupled with the fact that the distal needle section is rigidly fixed relative to the proximal needle portion, minimizes or eliminates the tendency of the distal needle section to bend, buckle or "noodle", as would likely occur using a significantly longer distal needle portion, particularly given the very small diameter of the distal needle portion. The tendency of the distal needle portion to noodle would also likely increase if the proximal and distal needle sections were not rigidly fixed together.

According to one embodiment, the proximal needle portion may be tapered at the interface with the distal needle portion so as to not provide an abrupt stop surface. This may be advantageous when it is desired for the proximal needle portion to be inserted part way through the space between the gums and tooth during insertion of the distal needle portion into intraligamentary tissue. According to one embodiment, the proximal needle portion can become progressively thicker toward the hub or other means of connecting the proximal needle portion to a syringe. Alternatively, only the portion of the proximal needle portion nearest the distal needle portion may be tapered.

Both the proximal and distal needle portions are advantageously rigid. The larger diameter of the proximal needle portion provides overall rigidity and strength to the two-part needle. The length of the proximal needle portion may be significantly longer than the distal needle portion (i.e., up to 50 mm, preferably between about 5 mm and about 30 mm). Limiting the overall length of the two-part needle limits the length-to-width aspect ratio of the needle, which can provide rigidity and strength to the overall needle device so as to facilitate piercing through very tough and dense ligamentary tissue without bending or buckling of either the proximal or distal portions.

The proximal needle portion is formed from a suitable rigid material, although metal is preferred. Forming the proximal needle portion of metal (e.g., stainless steel) provides for strength and rigidity while also minimizing brittleness characteristics that may be present with other materials. Ceramic and rigid polymers can also be used to make the proximal needle portion.

Forming the distal needle portion of a ceramic material (e.g., an organically modified ceramic) allows the distal needle portion be strong and rigid, even with very small diameters. A high hardness metal can also be used to form the distal needle portion, such as by an additive process (e.g., plating of progressive layers). Rigidity and strength are important as the distal needle portion is designed to be pushed into tough ligamentary tissue surrounding a tooth to be anesthetized.

According to one method, the two-part needle device may be manufactured by providing a proximal needle portion formed of a rigid material, e.g., steel, ceramic or rigid plastic, providing a distal needle portion formed of ceramic or a high hardness metal, and attaching the distal needle portion to the proximal needle portion (e.g., by inserting part of the distal needle section into the hollow interior of the proximal needle portion and then fixing the two together). Attachment may be accomplished by any suitable technique. Examples include one or more of an adhesive, laser welding, soldering, friction fit, or crimped joint. These provide a rigid, non-slidable telescoping engagement between the two portions, thereby preventing longitudinal relative movement of the proximal and distal needle portions.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention is directed to specialized two-part needle devices for administering a local anesthetic into tough, dense intraligamentary tissue surrounding a tooth. According to one embodiment, the two-part needle includes a proximal needle portion formed of a rigid material (e.g., metal, ceramic or rigid plastic) and a distal needle portion formed of rigid ceramic or high hardness metal. The distal needle portion has an exposed length not more than about 8 mm, and a maximum outside diameter not more than about 25 gauge. The proximal needle portion has an outer diameter at its distal most point that is greater than the outer diameter of the distal needle portion where the two intersect to form an abrupt stop surface. The abrupt step helps limit the depth of penetration of the needle through the tissue. Alternatively, the proximal needle portion can be tapered at the intersection in a manner so as to not provide an abrupt stop surface. It will be appreciated that the two-part needle device is not limited to any particular use and can be adapted to inject a fluid into tissues other than intraligamentary tissue surrounding a tooth.

II. Exemplary Two-Part Dental Intraligamentary Injection Needles

Figure 1A:
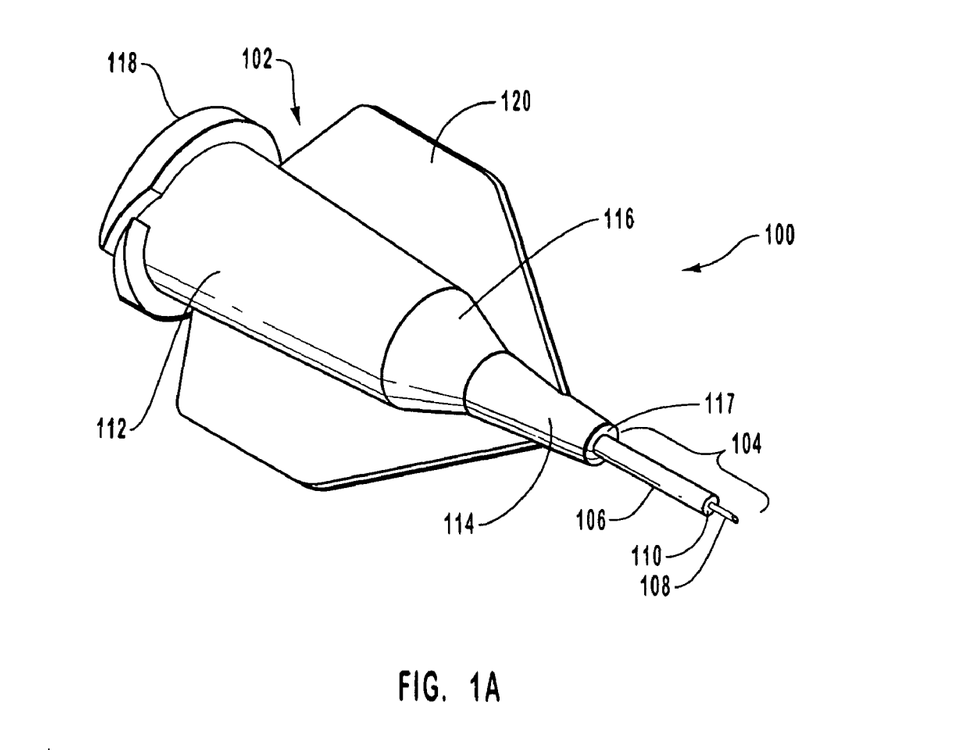
FIG. 1A illustrates a syringe-coupleable injection tip which includes an exemplary two-part needle.

FIG. 1A is a perspective view of an exemplary injection tip 100 that includes an exemplary two-part dental intraligamentary injection needle 104 according to one aspect of the invention. Injection tip 100 includes a hub 102 configured for coupling to a syringe or other fluid delivery device and a two-part needle 104 at a distal end of injection tip 100. Two-part needle 104 includes a proximal needle portion 106 and a distal needle portion 108 extending beyond a distal end of the proximal needle portion 106. In this embodiment, the distal needle portion 108 includes an embedded section disposed within the hollow interior of proximal needle portion 106 and an exposed section extending distally beyond proximal needle portion 106. Proximal needle portion 106 has an outside diameter that is larger than the outside diameter of the distal needle portion 108. In this embodiment, the transition between the smaller outside diameter of exposed distal needle portion 108 and larger outside diameter of proximal needle portion 106 is abrupt (i.e., not smoothly tapered), thereby advantageously forming an abrupt stop surface 110 at this transition. As discussed below, the proximal needle portion may alternatively be tapered at the intersection with the distal needle portion so to provide a more gradual transition between the distal and proximal needle portions rather than an abrupt stop surface (see FIGS. 4A and 4B).

Hub 102 has two primary components, including a body 112 and a neck 114. Neck 114 is illustrated as being tapered, although it can alternatively be untapered. Neck 114 is preferably narrower than body 112, as depicted. A tapered shoulder 116 may be present to provide a gradual transition from body 112 to neck 114.

A nib 117 disposed at the distal end of neck 114 around a proximal end of proximal needle portion 106 assists in retaining needle 104 within hub 102 and in providing a seal around proximal needle portion 106. Nib 117 may comprise an adhesive plug that has been cured after proximal needle portion 106 has been positioned within neck 114. Any suitable adhesive may be employed, such as for example commercially available epoxies intended for gluing stainless steel to plastics such as polypropylene. Alternatively, nib 117 may simply comprise a distal end of neck 114 (e.g., neck 114 may be molded around a proximal unexposed portion of proximal needle portion 106), so that nib 117 is formed from the same material as the remainder of neck 114.

Hub 102 is preferably designed to be coupled to a syringe or other fluid delivery device for dispensing fluid through needle 104. Hub 102 further includes a male or female thread or groove coupling member 118 (e.g., a luer lock structure), which mates with another thread and groove structure to engage injection tip 100 to a syringe or similar device. Hub 102 preferably includes structure that provides a gripping surface to aid in coupling injection tip 100 to a syringe. The illustrated example includes wings 120 extending longitudinally from body 112, although ridges or another gripping structure may alternatively be used. In a further alternative, the hub may be an integral extension of a device such as a syringe, such that neither coupling structure 118 nor gripping structures need be provided.

Proximal needle portion 106 of two-part needle 104 is advantageously formed of a rigid material. Examples of suitable materials include ceramic, rigid plastics, or metal, although metal is preferred. The material rigidity of the proximal portion may be as high as that of the distal needle portion 108, but may also be slightly less so long as it is sufficiently rigid to resist the torquing forces applied to the distal needle portion 108. For this reason, a metal material (e.g., stainless steel) is preferred for its ability to provide high strength and rigidity to proximal needle portion 106 without being brittle or easily deformable.

As illustrated, proximal needle portion 106 represents the majority of the overall length of needle 104. In order to firmly anchor the distal needle portion 108 to prevent bending, noodling, or dislodgement by compressive and/or torquing forces, the length of the proximal needle portion 106 can be sufficiently large relative to the exposed length of the distal needle portion 108 to reduce or eliminate any levering effect of the distal end. The length of the proximal needle portion that overlaps the embedded distal portion is preferably at least about 2 times the length of the exposed distal needle portion, more preferably at least about 4 times, and in some cases, it may be about 10 times longer or more. For example, proximal needle portion 106 may have a length between about 2 mm and about 50 mm, more preferably between about 5 mm and about 30 mm, and most preferably between about 7 mm and about 20 mm.

Also as shown, proximal needle portion 106 has an outside diameter that is significantly greater than the outside diameter of distal needle portion 108. The outside diameter of proximal portion 106 should be selected to provide at least two benefits: (1) provide sufficient strength and rigidity to firmly anchor and hold the distal needle portion 108 during use and (2) to provide sufficient diameter to provide a stop surface 110 that is able to limit penetration to substantially only the distal needle portion 108. At least the portion of the proximal needle portion 106 that surrounds an embedded portion of the distal needle portion 108 has an inner diameter that is substantially the same as the outer diameter of the distal needle portion 108. This helps prevent lateral movement by the distal needle portion 108 and buckling. In general, the outer diameter of the proximal needle portion 106 is equal to two times the wall thickness plus the inner diameter. Proximal needle portion 106 preferably has a wall thickness that is at least about 5% of the inner diameter of the proximal needle portion, preferably at least about 10%, more preferably at least about 15%, and most preferably at least about 50% of the inner diameter. In some cases the wall thickness can be at least about 100%, or even at least about 500% of the inner diameter.

As illustrated, proximal needle portion 106 may be cylindrical in shape, e.g., it may have a substantially constant outside diameter (e.g., a single telescoping arrangement with distal needle portion 108). Alternatively, multiple telescoping proximal needle portions can be provided having progressively increasing diameters moving proximally away from the intersection between the proximal portion 106 and distal portion 108. The proximal needle portion can have other cross-sectional shapes, such as oval, square, rectangular, pentagonal, hexagonal, and the like.

In embodiments that include an abrupt stop surface, the outside diameter of the proximal needle portion is preferably between about 10% and about 1000% greater than the maximum outside diameter of the distal needle portion 108 at the transition between the distal needle portion 108 and the proximal needle portion 106. More preferably, the outside diameter of the proximal needle portion is between about 20% and about 700% greater than the maximum outside diameter of the distal needle portion 108 at the transition between the distal needle portion 108 and the diameter proximal needle portion 106. Most preferably, the outside diameter of the proximal needle portion is between about 30% and about 200% greater than the maximum outside diameter of the distal needle portion 108 at the transition between the distal needle portion 108 and the proximal needle portion 106 where it is desired to have an abrupt stop surface.

Distal needle portion 108 of two-part needle 104 may advantageously be formed of a ceramic material (e.g., an organically modified ceramic) so as to provide rigidity and strength to the distal needle portion, even with its very small dimensional characteristics. Exemplary organically modified ceramic materials are available from Fraunhofer-Gescllschaft, in Munich Germany. Details regarding such materials and methods of forming micro-needles therefrom are described in TWO PHOTON POLYMERIZATION OF POLYMER-CERAMIC HYBRID MATERIALS FOR TRANSDERMAL DRUG DELIVERY, Int. J. Appl. Ceram. Technol., 4 [1] 22-29 (2007), which is incorporated herein by specific reference.

As disclosed in the foregoing article, ceramic micro-needles formed from organically modified ceramic materials were formed using a two photon polymerization (2PP) process involving both temporal and spatial overlap of photons to induce chemical reactions leading to photopolymerization and material hardening within well-defined highly localized volumes. The desired three-dimensional needle structures produced by polymerizing the material along a laser trace, which is moved in three dimensions using a galvano-scanner and a micropositioning system. The material outside the desired region does not participate in the reaction and can be washed away with an appropriate alcohol solution, e.g., to form a hole in the needle.

It may also be possible to form the distal needle portion 108 from a high hardness metal material, such as by an additive plating process. As noted above, distal needle portion 108 provides only a fraction of the overall length of needle 104. Distal needle portion 108 preferably has a maximum exposed length of about 8 mm, and preferably an exposed length between about 1 mm and about 8 mm, more preferably between about 2 mm and about 6 mm, and most preferably between about 25 mm and about 5 mm. As noted above, distal needle portion 108 has a maximum outside diameter that is significantly smaller than the maximum outside diameter of proximal needle portion 106. Distal needle portion 108 preferably has a maximum outside diameter of 25 gauge, preferably between about 28 and about 38 gauge, more preferably between about 30 and 35 gauge, and most preferably between about 31 and 35 gauge.

In general, a needle having an abrupt stop will require a larger distal needle portion to penetrate into the intraligamentary tissue, as the stop inhibits insertion of the proximal needle portion between the gums and the tooth. Conversely, a more extreme taper permits for shorter distal needle portion lengths because at least the initial tapered section of the proximal needle portion can function as a needle by penetrating between the gums and the tooth.

The small dimension of the distal needle portion results in nearly pain free penetration of the two-part needle into the gingiva and into the very tough and dense ligamentary tissue. The short length of the exposed distal needle portion minimizes the tendency of distal needle portion 108 to buckle, bend, noodle, or act as a lever when pushing the very short distal needle portion 108 into the ligamentary tissue. The longer length proximal needle portion 106, with its accompanying larger diameter, provides necessary working length for the needle to be maneuvered around the teeth and surrounding oral structure, while also providing sufficient strength and rigidity to the overall needle 104 so as to prevent the needle from bending or buckling during use.

Figure 1B:
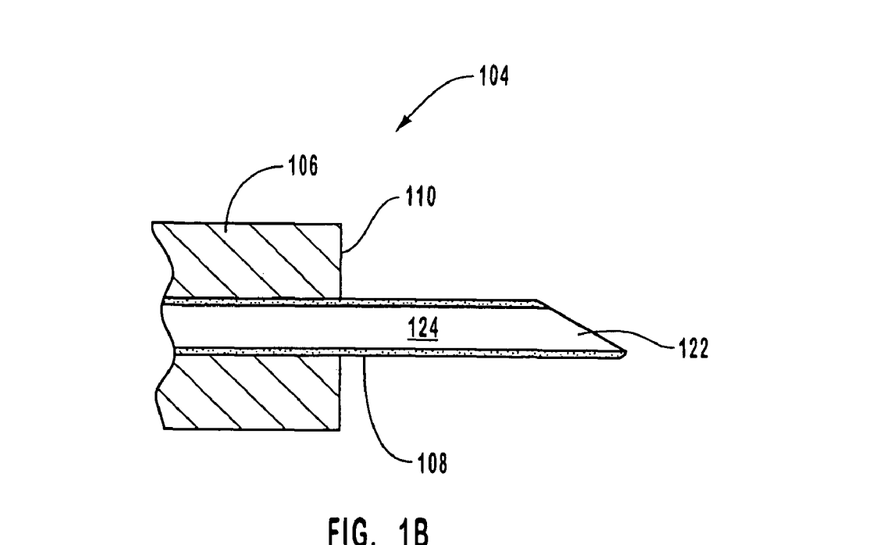
FIG. 1B illustrates a close up cross-sectional view of the distal portion and stop surface of the two-part needle device of the injection tip of FIG. 1A.

As shown in FIG. 1B, an embedded section of the distal needle portion 108 is embedded within the interior of proximal needle portion 106. The embedded section of distal needle portion 108 can extend partially through the interior of the proximal needle portion 106, all the way through proximal needle portion 106, or beyond the hub 102 in order to permit puncture of a membrane of an anesthetic carpule, e.g., as used in reusable, autoclavable metal syringes with disposable tips and needles. In general, the embedded section of distal needle portion 108 should extend within the proximal needle portion 106 a sufficient amount to provide secure engagement between the proximal needle portion 106 and distal needle portion 108. For example, the embedded section of distal needle portion may extend at least about 2 mm, or at least about 10 mm through the interior of proximal needle portion 106.

As perhaps best seen in FIG. 1B, the piercing tip 122 of distal needle portion 108 may be beveled so as to form a sharp point at tip 122. Although illustrated with a beveled configuration, alternative tip configurations may be used. Distal needle portion 108 includes an interior lumen 124, which is in fluid communication with an adjacent lumen (not shown) through proximal needle portion 106, which is in fluid communication with an internal chamber (not shown) of hub 102, including neck 114. In the illustrated embodiment, an unexposed, embedded portion of distal needle portion 108 extends proximally within proximal needle portion 106 beyond the stop surface 110. The two portions may be joined together by any suitable means, for example, an adhesive, laser welding, soldering, a friction fit, or a crimped joint so as to form a rigid, non-slidable connection.

Figure 2A:
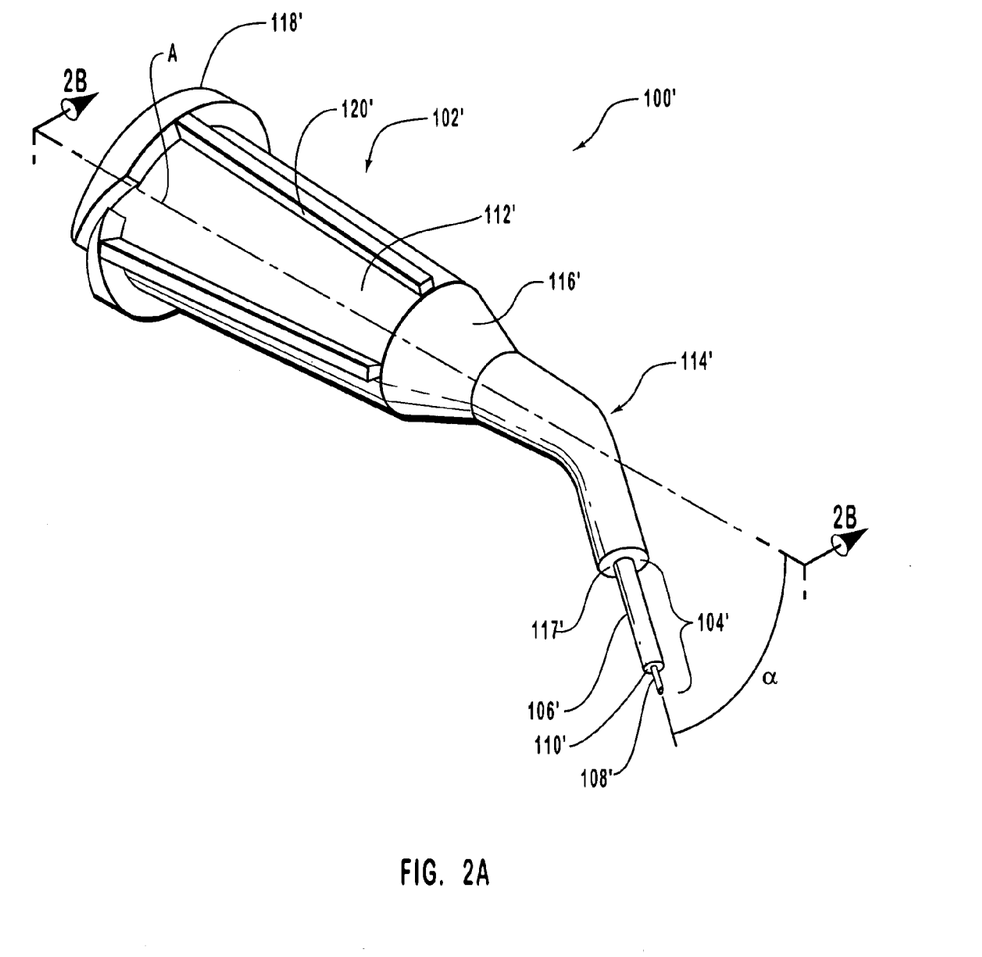
FIG. 2A illustrates an alternative example of a syringe coupleable injection tip including a two-part needle.
Figures 2B, 2C:
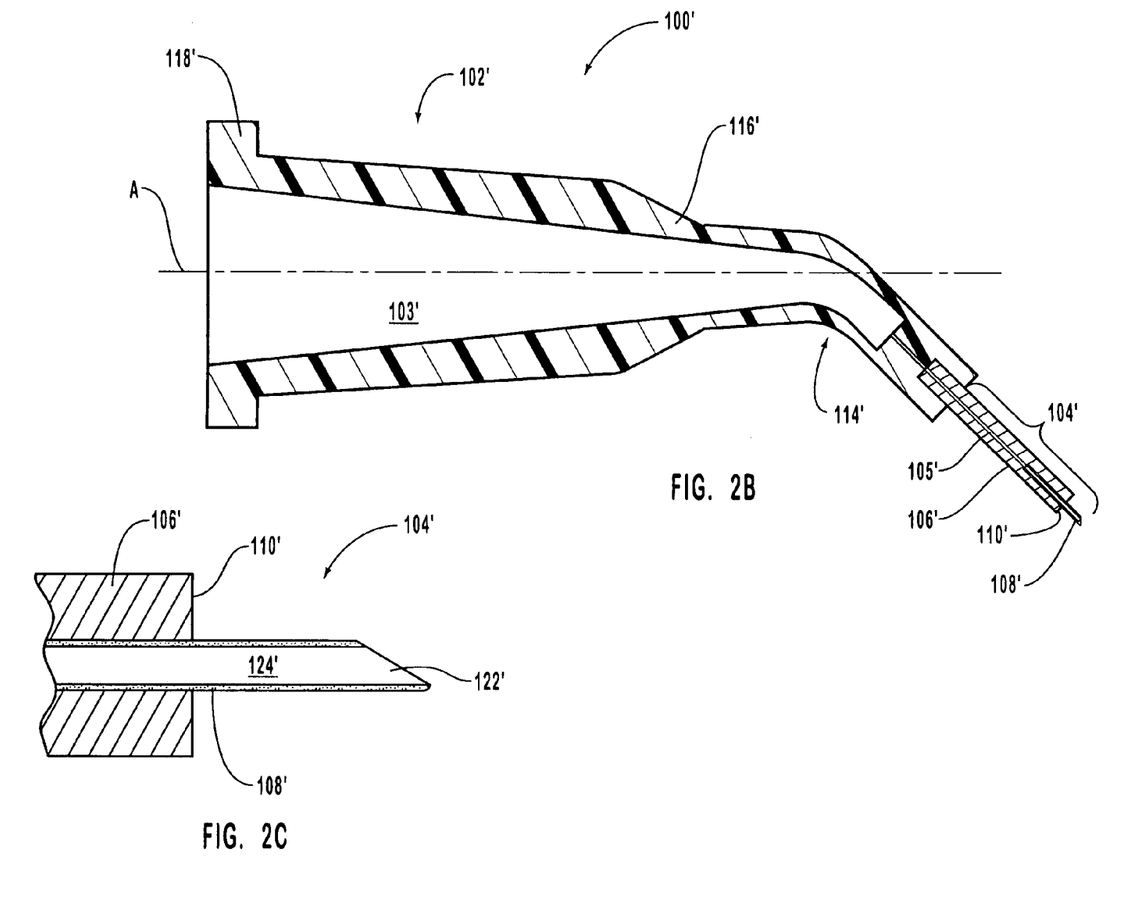
FIG. 2B illustrates a cross-sectional view of the injection tip of FIG. 2A.
FIG. 2C illustrates a close up cross-sectional view of the distal portion and step surface of the two-part needle of the injection tip of FIGS. 2A and 2B.

FIGS. 2A-2C illustrate an alternative exemplary syringe coupleable injection tip 100' similar to injection tip 100, including a hub 102', chamber 103' (FIG. 2B), a body 112', a neck 114', a shoulder 116', a nib 117', lumens 105' and 124', and coupling structure 118'. One difference between device 100' and device 100 is the presence of a plurality of ridges 120' rather than wings 120 to aid in gripping the hub 102' while coupling to a syringe or other fluid delivery device.

Figure 5A:
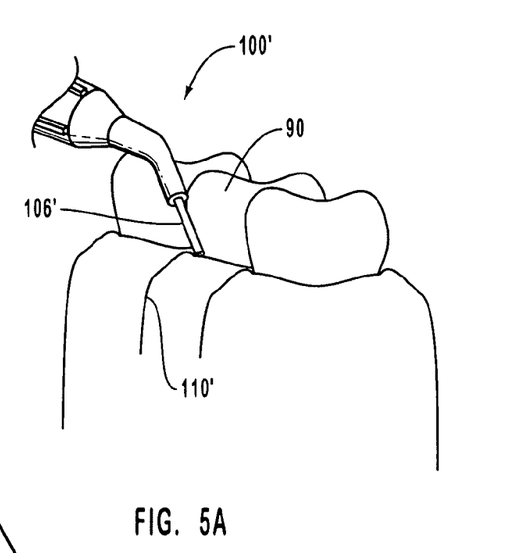
FIG. 5A illustrates a perspective view of the injection tip of FIGS. 2A-2C being used to inject a local anesthetic into dense, tough ligamentary tissue adjacent to a tooth.

Another difference between device 100' and device 100 of FIGS. 1A-1B is that injection tip 100' includes a needle 104' that is angled with respect to longitudinal axis A'. Preferably, the angle α is in the range of about 15° to about 90°, more preferably about 20° to about 70°, and most preferably about 30° to about 60°. In the embodiment shown in FIGS. 2A-2B, the angle α is about 60°. The angle ranges, particularly the most preferred range, advantageously enables a practitioner to maneuver the tip 104' without interference from adjacent structures near the injection area (e.g., the particular tooth to be anesthetized and/or adjacent teeth). For example, as shown in FIG. 5A, injection tip 100' can be moved comfortably and easily into position adjacent to tooth 90 without any unintended contact with tooth 90, the teeth of the opposite jaw by the practitioner's hand, an attached syringe, or coupled injection tip 100'. In other words, such an angled configuration aids in positioning the bulk of the injection tip 104', an attached syringe, and the practitioner's gripping hand out of the way of the injection site.

Figure 3A:
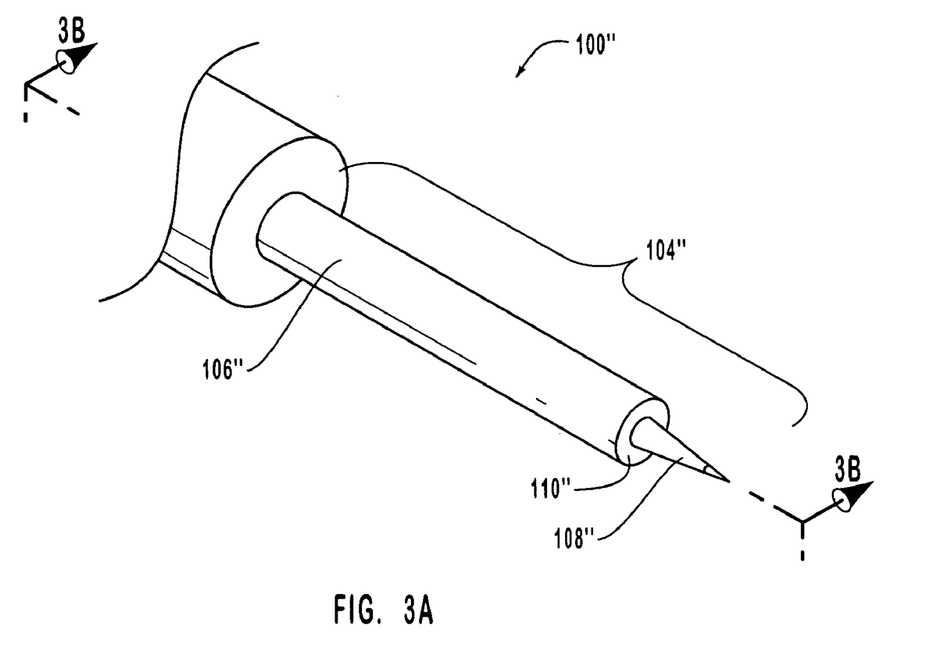
FIG. 3A illustrates another exemplary injection tip device including an alternative example of a two-part needle.
Figure 3B:
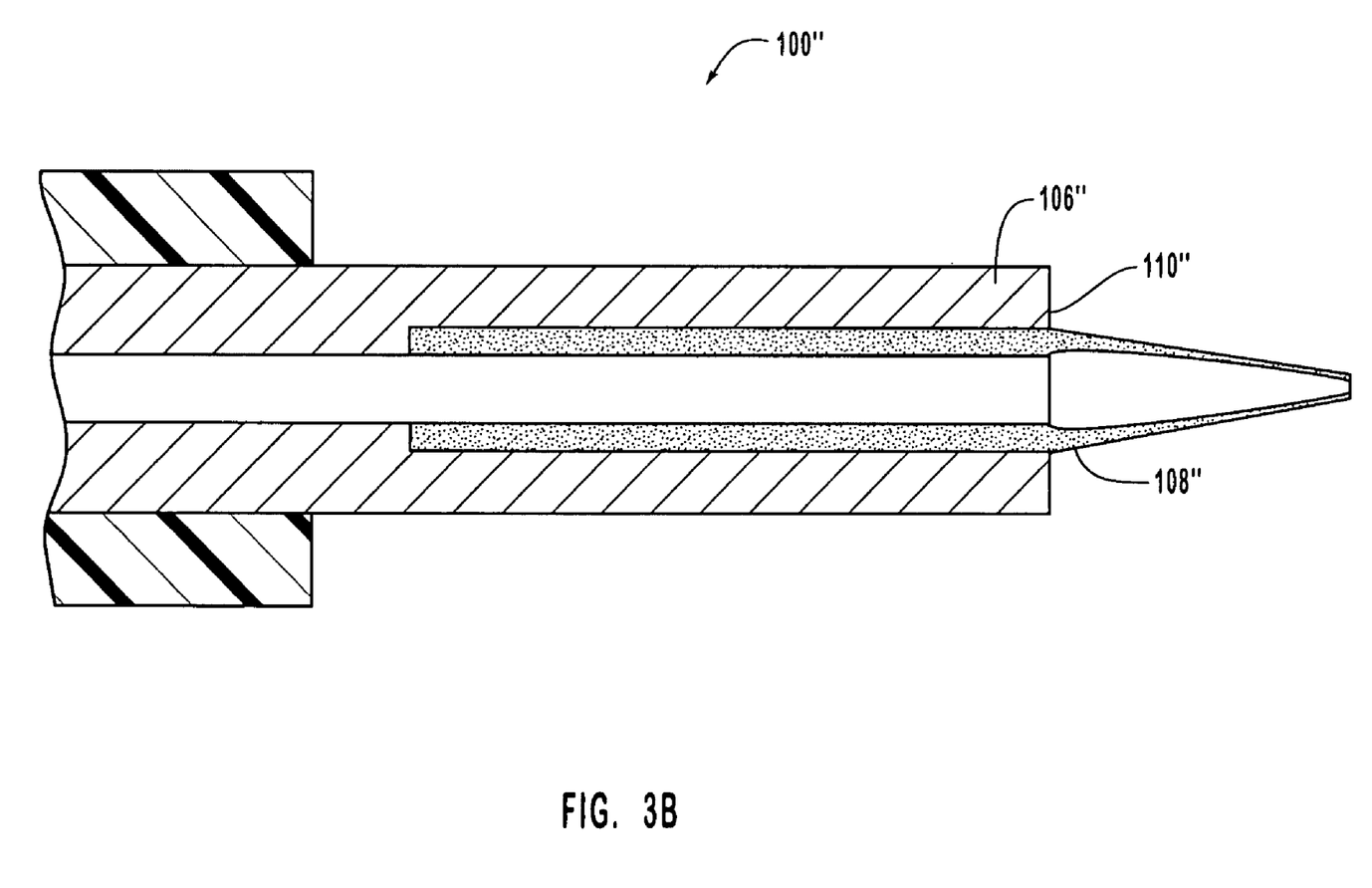
FIG. 3B illustrates a close up cross-sectional view of a portion of the two-part needle device of the injection tip of FIG. 3A.

FIGS. 3A-3B illustrate the distal end of another alternative injection tip 100" similar to devices 100 and 100'. One difference relative to device 100" is that needle 104" is illustrated as including a proximal needle portion 106" and a distal needle portion 108" in which the exposed part of distal needle portion 108" is generally conical in shape, rather than including an outside diameter which is substantially constant along the entire exposed length of distal needle portion 108". As shown, there is an abrupt stop surface 110" designed to prevent excessive penetration of the two-part needle 104" into the tissue during injection of a local anesthetic into ligamentary tissue. Because it is advantageously formed of ceramic, the extreme distal tip of distal needle portion 108 may be considerably smaller than maximum outside diameter 0.5 mm (e.g., 0.1 mm) without unnecessarily compromising strength and rigidity, while still being commercially practicable from a manufacturing perspective. In other words, it can be impractical if not nearly impossible to form such a distal needle portion from metal or other materials with such small dimensional characteristics while maintaining desired properties of strength and rigidity.

As illustrated in the previous examples, the transition between the proximal needle portion and the distal needle portion may be perpendicular to the exterior wall of the distal needle portion to form an abrupt stop surface. Nevertheless, it will be appreciated that the stop surface can be provided by other angles (e.g., between about 60° and 150°). Alternatively, the taper angle of the proximal needle portion at the intersection with the distal needle portion may be so high as to not provide any stop surface (e.g., between about 150° and about 179°, or between about 160° to about 175°). In such a case, the tapered distal end of the proximal needle portion may act as a needle that can also penetrate into the space between the gums and the tooth.

Figure 4A:
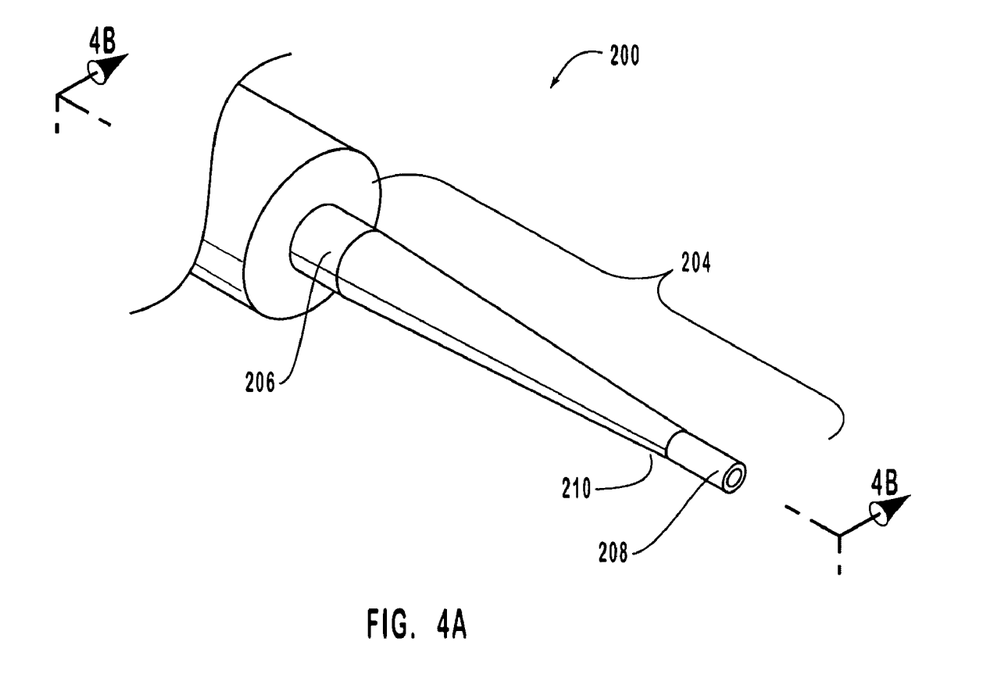
FIG. 4A illustrates another exemplary injection tip including an alternative example of a two-part needle.
Figure 4B:
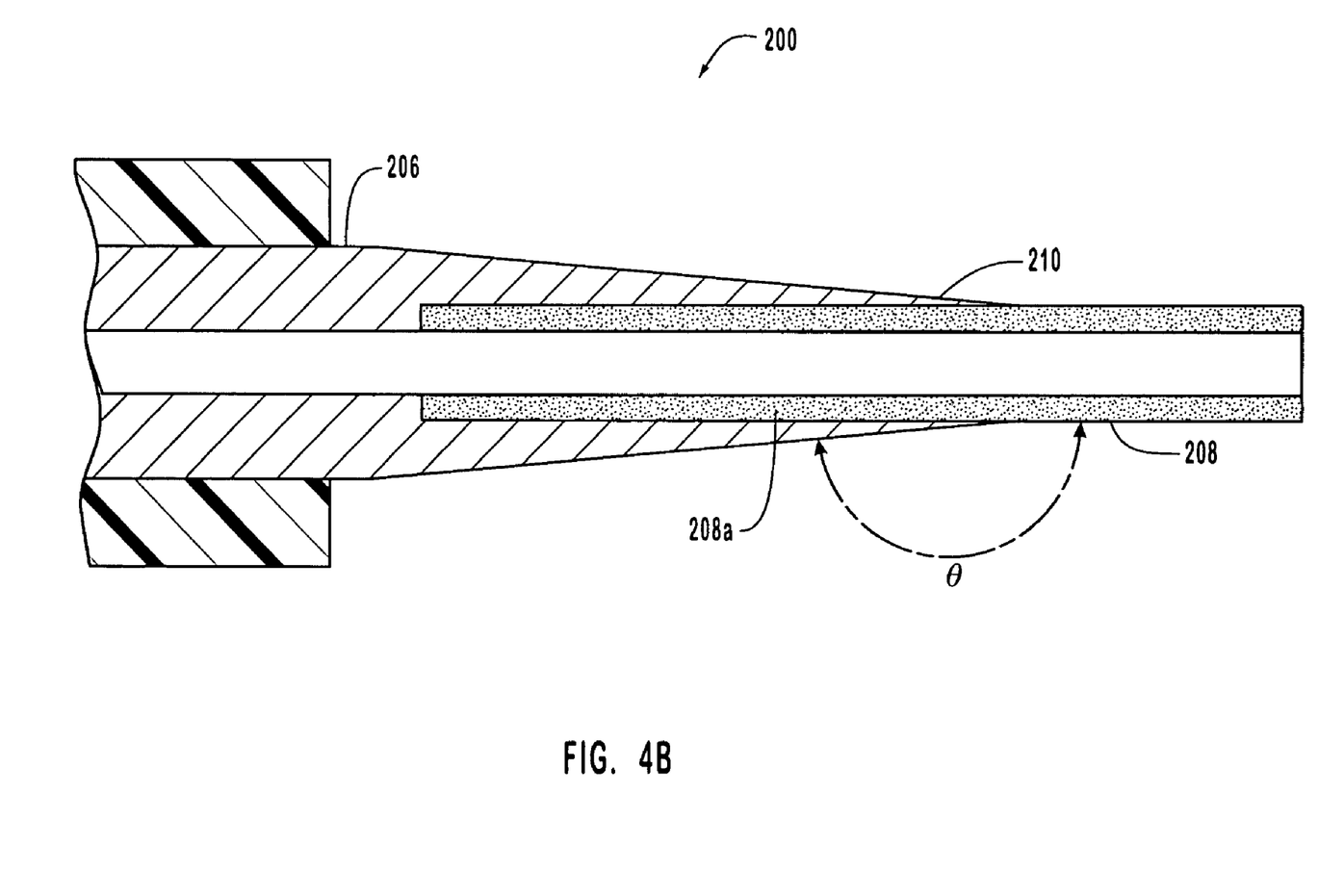
FIG. 4B illustrates a close up cross-sectional view of a portion of the two-part needle device of the injection tip of FIG. 4A.

By way of example, FIGS. 4A and 4B illustrate an alternative device 200 similar to devices 100 and 100'. The principal difference of device 200 is that the two-part needle 204 is illustrated as including a proximal needle portion 206, a distal needle portion 208, and a tapered surface 210 having an angle θ (e.g., about 175°) so as to provide no stop surface. This permits penetration by at least the tapered surface 210 of proximal needle portion 206 into tissue (e.g., between the gums and tooth) during injection of a local anesthetic into ligamentary tissue. This, in turn, permits deeper penetration of distal needle portion 208 beyond its actual length into the tissue. In general, all or part of the proximal needle can be tapered. Moreover, the taper can be continuous or changing (e.g., so as to form a concave or convex transition surface 210).

Figure 5B:
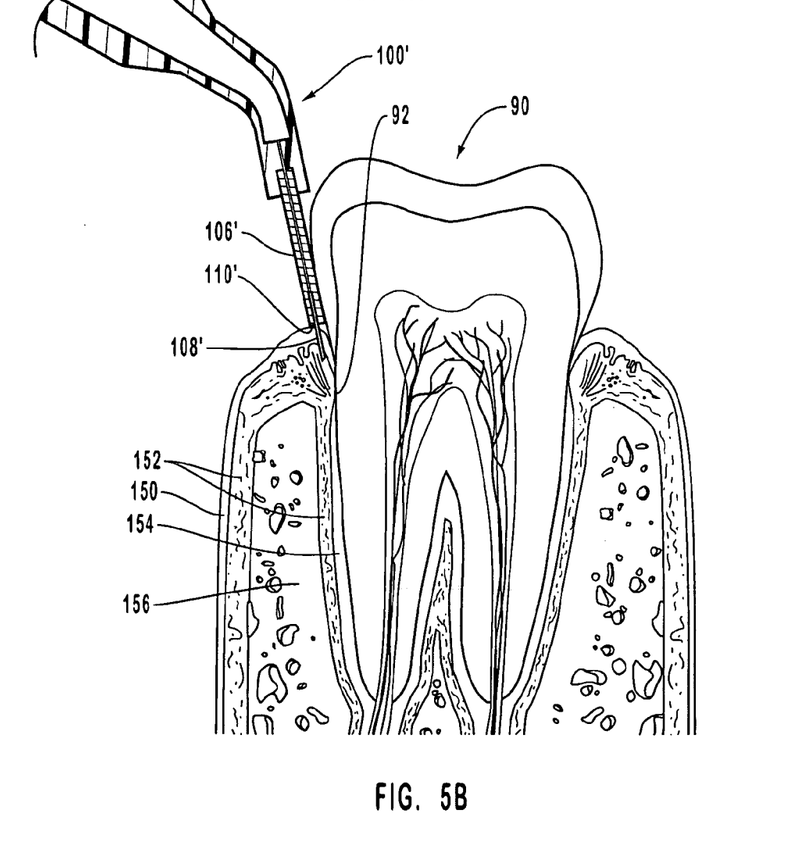
FIG. 5B illustrates a partial cross sectional view of FIG. 5A, showing penetration of the distal needle portion through the gingiva and into the ligamentary tissue, with the stop surface being positioned against the exterior surface of gingival tissue so as to limit or prevent piercing of the larger proximal portion into the patient's tissue.
Figure 5C:
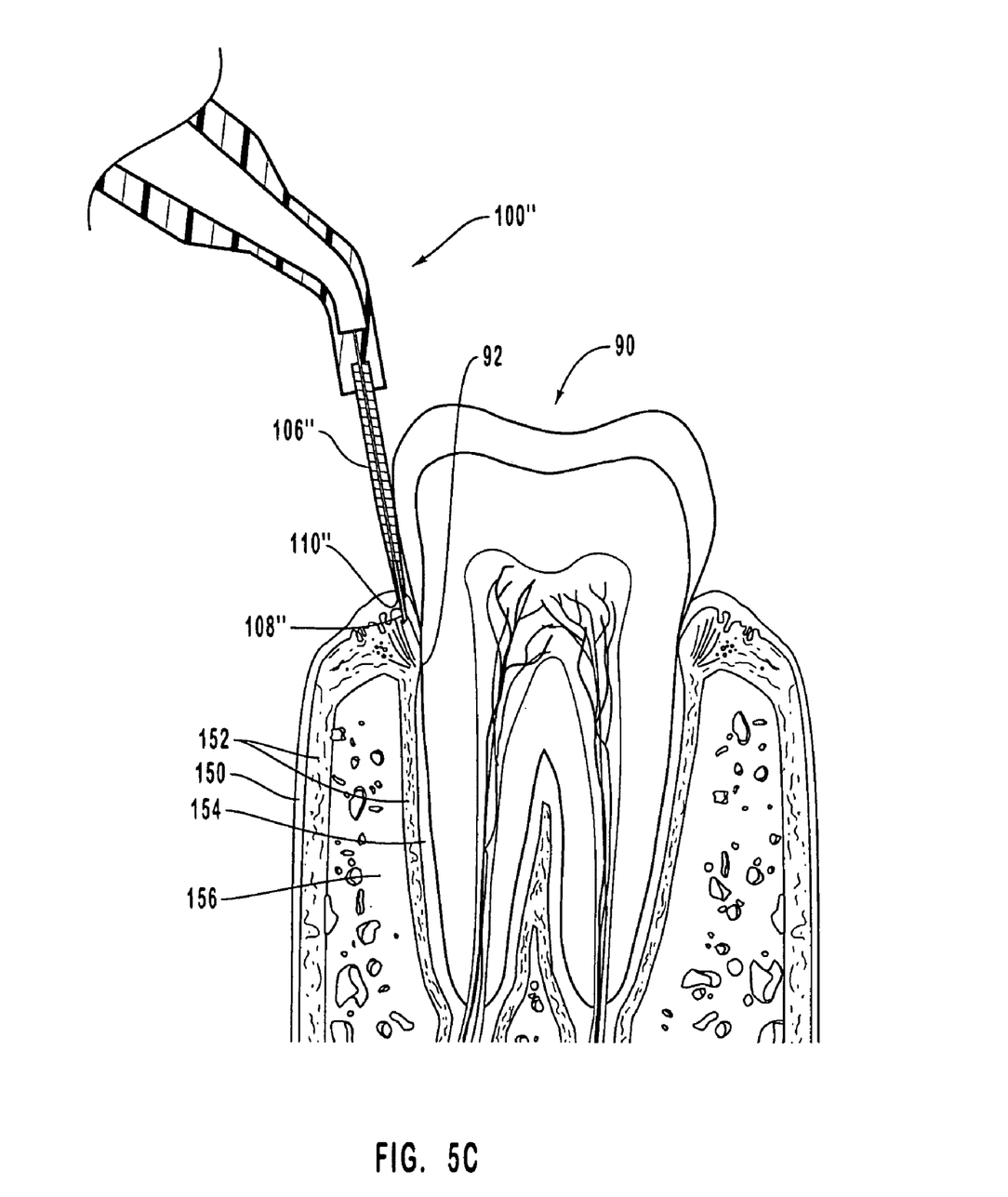
FIG. 5C illustrates a partial cross sectional view of an alternative injection tip similar to the embodiment shown in FIGS. 4A and 4B, with the forward end of the tapered surface of the proximal needle portion penetrating through soft gingival tissue adjacent to the tooth.

FIGS. 5A-5C illustrates how two-part needles according to the invention can be used to inject a local anesthetic into intraligamentary tissue surrounding a tooth. Examples of useful local anesthetics include, but are not limited to, lidocaine, tetracaine, benzocaine, chloroprocaine, cocaine, cyclomethycine, demethocaine, propoxycaine, procaine, proparacaine, articaine, bupivacaine, carticaine, cinchocaine, etidocaine, levobupivacaine, mepivacaine, and piperocaine.

The two-part needle of provides sufficient rigidity so as to prevent bending or buckling of the two-part injection needle 104' (FIGS. 5A and 5B) or 104" (FIG. 5C), while also minimizing pain through use of a small diameter, short distal needle portion 108', which penetrates through gingival tissue 150 and into ligamentary tissue 152. According to the embodiment shown in FIGS. 5A and 5B, the distal needle portion 108' is inserted in the space between the gums and tooth. The stop surface 110' aids a practitioner in easily injecting a local anesthetic into the ligamentary tissue 152 adjacent gum tissue 150. This configuration prevents excessive penetration of the distal needle portion 108' so as to prevent penetration into bone tissue 156, the cementum 154, and/or the root of tooth 90. Excessive penetration (e.g., into cementum 154 or root of tooth 90) can result in unnecessary damage to the tooth and severe pain to the patient as a result of the presence of very sensitive nerve tissue deep within the tissue adjacent to the tooth.

Stop member 110' rests adjacent the exterior gingival tissue 150 when distal needle portion 108' is fully inserted into the ligamentary tissue. Stop member 110' substantially limits or prevents proximal needle portion 106' from piercing through the patient's soft tissue, which greatly minimizes the sensation of pain during penetration by distal needle portion 108'. Proximal needle portion 106' does, however, lend substantial strength and rigidity to the overall needle structure while also providing for sufficient working length so as to allow for easy maneuvering of the device 100' adjacent to tooth 90.

In alternative method of use shown in FIG. 5C, a two-part needle having a tapered proximal needle portion (e.g., as in FIGS. 4A and 4B) may permit insertion of at least the narrowest portion of tapered surface 110" of the tapered proximal needle portion 106" through soft gingival tissue 150 and/or between the gums and tooth 90. In such a case, it may be beneficial to utilize a shorter distal needle portion 108" to prevent excessive penetration of the distal needle portion 108" (e.g., to prevent damage as noted above).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A micro-needle device for administering a local anesthetic to tissue, comprising:
    a proximal needle portion formed of a ceramic or metal and having an outside diameter, a hollow interior, a distal end surface, and a length;
    a distal needle portion formed of ceramic or metal extending from the distal end surface of the proximal needle portion and having an outside diameter that is less than the outside diameter of the proximal needle portion, wherein the distal needle portion is rigidly disposed relative to the proximal needle portion, extends beyond the distal end of the proximal needle portion by a length of not more than about 8 mm, and has an outside diameter less than about 25 gauge; and
    an abrupt stop surface provided by the distal end surface of the proximal needle portion that limits penetration of the micro-needle device through tissue beyond the abrupt stop surface.

2. A micro-needle device as in claim 1, the distal needle portion further comprising an embedded section that extends at least partially through the hollow interior of the proximal needle portion.

3. A micro-needle device as defined in claim 1, wherein the proximal needle portion has a wall thickness at the abrupt stop surface that is at least about 5% greater than an interior diameter of the proximal needle portion at the abrupt stop surface.

4. A micro-needle device as defined in claim 1, wherein the proximal needle portion has a wall thickness at the abrupt stop surface that is at least about 15% greater than an interior diameter of the proximal needle portion at the abrupt stop surface.

5. A micro-needle device as defined in claim 1, wherein the proximal needle portion has a wall thickness at the abrupt stop surface that is at least about 50% greater than an interior diameter of the proximal needle portion at the abrupt stop surface.

6. A micro-needle device as defined in claim 1, wherein the length of the proximal needle portion is between about 2 mm and about 50 mm.

7. A micro-needle device as defined in claim 1, wherein the length of the proximal needle portion is between about 5 mm and about 30 mm.

8. A micro-needle device as defined in claim 1, wherein the length of the proximal needle portion is between about 7 mm and about 20 mm.

9. A micro-needle device as defined in claim 1, wherein the proximal needle portion is formed from metal and the distal needle portion is formed from ceramic.

10. A micro-needle device as defined in claim 1, wherein the distal needle portion has an outside diameter between about 28 gauge and about 38 gauge.

11. A micro-needle device as defined in claim 1, wherein the distal needle portion has an outside diameter between about 30 gauge and about 35 gauge.

12. A micro-needle device as defined in claim 1, wherein the distal needle portion extends beyond the distal end of the proximal needle portion with a length between about 1 mm and about 8 mm.

13. A micro-needle device as defined in claim 1, wherein the distal needle portion extends beyond the distal end of the proximal needle portion with a length between about 2 mm and about 6 mm.

14. A micro-needle device as defined in claim 1, wherein the distal needle portion extends beyond the distal end of the proximal needle portion with a length between about 2.5 mm and about 5 mm.

15. A micro-needle device as defined in claim 1, wherein the outside diameter of the proximal needle portion is between about 100% and about 1000% larger than the outside diameter of the distal needle portion.

16. A micro-needle device as defined in claim 1, wherein the outside diameter of the distal needle portion is substantially constant.

17. A micro-needle device as defined in claim 1, wherein the distal needle portion is tapered.

18. A micro-needle device for administering a local anesthetic to tissue, comprising:
  a proximal needle portion formed of a rigid material and having an outside diameter, a hollow interior, and a length;
  a distal needle portion formed of ceramic or metal and rigidly affixed to the proximal needle portion,
    the distal needle portion having an embedded section which extends at least partially through the hollow interior of the proximal needle portion and an exposed penetrating section extending from a distal end of the proximal needle portion,
    at least a portion of the embedded section being rigidly affixed to the hollow interior of the proximal needle portion,
    the exposed penetrating section of the distal needle portion having a length of not more than about 8 mm and an outside diameter less than about 25 gauge; and
  an abrupt stop surface at a transition between the exposed penetrating section of the distal needle portion and the distal end of the proximal needle portion for limiting penetration of the micro-needle device through tissue.

19. A micro-needle device as defined in claim 18, wherein the distal needle portion has an outside diameter of 30 gauge or less.

20. A micro-needle device for administering a local anesthetic to tissue, comprising:
  a proximal needle portion formed of a metal or ceramic and having an outside diameter, a hollow interior, and a length; and
  a distal needle portion formed of ceramic or metal and rigidly affixed to the proximal needle portion,
    the distal needle portion having an embedded section which extends at least partially through the hollow interior of the metal or ceramic proximal needle portion and an exposed penetrating section extending from a distal end of the metal or ceramic proximal needle portion,
    at least a portion of the embedded section being rigidly affixed to the hollow interior of the metal or ceramic proximal needle portion,
    the exposed section of the distal needle portion having a length of not more than about 8 mm and an outside diameter less than about 25 gauge.

21. A method of manufacturing a micro-needle device for administering a local anesthetic to tissue, comprising:
  providing a proximal needle portion formed of a rigid material and having an outside diameter and a hollow interior having an inner diameter; and
  rigidly affixing a distal needle portion formed of ceramic or a metal to the proximal needle portion by inserting the distal needle portion into the proximal needle portion so that the distal needle portion comprises an embedded section within the proximal needle portion in a manner so as to eliminate any space between the distal needle portion and the proximal needle portion at a transition between the distal needle portion and the proximal needle portion,
  the distal needle portion having an outside diameter that is smaller than an outside diameter of the proximal needle portion so that a transition from the smaller outside diameter of the distal needle portion to the outside diameter of the proximal needle portion forms an abrupt stop surface to limit penetration of the micro-needle device through tissue beyond the abrupt stop surface during use;
  the distal penetrating needle portion having an exposed length less than about 8 mm and an exposed maximum outside diameter of about 25 gauge.

22. A method of manufacturing as defined in claim 21, wherein the distal needle portion is rigidly affixed to the proximal needle portion by one of an adhesive, laser welding, soldering, friction fit, or crimped joint.

23. A micro-needle device as in claim 1, wherein the proximal needle portion and the distal needle portion comprise separate pieces that are rigidly affixed together by at least one of an adhesive, laser welding, soldering, friction fit, or crimped joint.

24. A micro-needle device as in claim 18, wherein the embedded section of the distal needle portion is rigidly affixed to the proximal needle portion by one of an adhesive, laser welding, soldering, friction fit, or crimped joint.

25. A micro-needle device as in claim 20, wherein the embedded section of the distal needle portion is rigidly affixed to the proximal needle portion by one of an adhesive, laser welding, soldering, friction fit, or crimped joint.

26. A micro-needle device for administering a local anesthetic to tissue, comprising:
  a hub portion for attachment to a syringe, the hub portion having a proximal end and a distal end;
  an outer sleeve portion formed of a rigid material and having an outside diameter, a hollow interior, a length, a proximal end attached to the hub portion, and a distal end;
  a needle portion formed of ceramic or metal, having an outer diameter that is less than the outside diameter of the outer sleeve portion, and being rigidly affixed relative to the outer sleeve portion,
    the needle portion having an embedded section which extends at least partially through the hollow interior of the outer sleeve portion and an exposed tissue penetrating section which extends from the distal end of the outer sleeve portion, the exposed tissue penetrating section of the needle portion having a length of not more than about 8 mm and an outside diameter less than about 25 gauge.

27. A micro-needle device as in claim 26, wherein the embedded section of the needle portion is rigidly affixed relative to the outer sleeve portion by at least one of an adhesive, laser welding, soldering, friction fit, or crimped joint.

28. A micro-needle device as in claim 20, further comprising an abrupt stop surface at a transition between the distal needle portion and the distal end of the proximal needle portion for limiting penetration of the micro-needle device through tissue.

29. A micro-needle device as in claim 20, further comprising a tapered surface at a transition between the exposed penetrating section of the distal needle portion and the proximal needle portion that permits penetration of at least a portion of the tapered surface through tissue.

30. A micro-needle device as in claim 28, the tapered surface having an angle relative to the distal needle portion between about 150° and about 179°.

31. A micro-needle device as in claim 28, the tapered surface having an angle relative to the distal needle portion between about 160° and about 175°.

* * * * *

UNITED STATES PATENT AND TRADEMARK OFFICE
CERTIFICATE OF CORRECTION

Page 1 of 2

PATENT NO.         : 8,398,397 B2
APPLICATION NO.    : 12/398039
DATED              : March 19, 2013
INVENTOR(S)        : Fischer It is certified that error appears in the above-identified patent and that said Letters Patent is hereby corrected as shown below:

In the Drawings
Sheet 8, replace Figure 5A with the figure depicted below, wherein incorrect reference number 110' and line have been removed

FIG. 5A

In the Specification
Column 3
Line 39, change "portion be" to --portion to be--

Signed and Sealed this
Eighteenth Day of February, 2014

Michelle K. Lee
*Deputy Director of the United States Patent and Trademark Office*

Column 4
Line 61, change "step" to --stop--

Column 7
Line 35, change "25 mm" to --2.5 mm--

Column 8
Line 67, change "108" to --108"--

Column 9
Line 36, change "illustrates" to --illustrate--
Line 44, change "needle of" to --needle--